United States Patent [19]
Hardy, Jr.

[11] 3,974,835
[45] Aug. 17, 1976

[54] ANASTOMOTIC APPARATUS AND METHOD

[76] Inventor: Thomas G. Hardy, Jr., 350 E. Broad St., Columbus, Ohio 43215

[22] Filed: Dec. 26, 1974

[21] Appl. No.: 536,325

[52] U.S. Cl.............................. 128/334 C; 285/260; 285/370; 285/397
[51] Int. Cl.²......................................... A61B 17/11
[58] Field of Search............ 128/334 R, 334 C, 335, 128/348; 285/260, 370, 397

[56] References Cited
UNITED STATES PATENTS

| | | | |
|---|---|---|---|
| 2,638,901 | 5/1953 | Sugarbaker | 128/334 C |
| 3,166,072 | 1/1965 | Sullivan | 128/334 C |
| 3,254,650 | 6/1966 | Collito | 128/334 C |
| 3,496,939 | 2/1970 | Odiaga | 128/334 R |

*Primary Examiner*—Dalton L. Truluck

[57] ABSTRACT

An apparatus for intestinal anastomosis is formed from a pair of anastomotic ring members, each of which is secured to the free end of two tubular tissue members to be anastomosed, and a coupling tube of special design adapted to join each ring member and its associated attached tissue member to the other ring member and attached tissue member. A method for performing intestinal anastomotic surgery utilizing the apparatus above wherein each tubular tissue member end is pulled over the outside and through the inside of one of the ring members and thereby inverted as it is secured to fenestrated projections on the ring member.

3 Claims, 7 Drawing Figures

ANASTOMOTIC APPARATUS AND METHOD

This is a substitute application of prior application Ser. No. 310,922 filed Nov. 30, 1972, now abandoned.

BACKGROUND, BRIEF SUMMARY AND OBJECTIVES OF THE INVENTION

Surgery requiring the union between parts of intestines, blood vessels or other hollow organs of a human body has long been a problem since it is usually performed by simply suturing together the free ends of the two tissue tubular members that are to be joined. This is time-consuming and sometimes impossible because of the anatomical position. In addition, complications such as a leak or obstruction at the suture line occasionally occur.

The present invention has been designed to improve anastomotic surgery and to make possible surgery of this nature in cases where it was therefore difficult or impossible to perform. It has particular application in all types of gastro-intestinal surgery including esophagogastrostomy, gastroduodenostomy and gastrojejunostomy as well as large and small bowel anastomosis.

The invention, in preferred form, includes a pair of anastomotic ring members having a plurality of fenestrated projections about their peripheries and a coupling tube having a convex outer surface, a concave inner surface and an opening substantially coincident with its longitudinal axis. Some means, usually suture material, is used to connect the free end of each of two tubular members to be anastomosed which is pulled over the outside and through the inside of the ring member and thereby inverted. The device will be constructed of a material that will disintegrate in two-three weeks.

It is therefore an objective of the present invention to provide a device that will permit a simple, rapid anastomosis.

Another objective of the present invention is to make possible simple anastomosis in parts of the body which would normally be quite time-consuming, difficult and/or impossible.

A further objective of the present invention is to provide anastomotic rings and a connecting device which can be formed of a composite material that will disintegrate within a specified period of time.

Yet another objective of the present invention is to provide anastomotic apparatus that is easily handled, inexpensive and capable of being stocked in operating rooms in quantities for immediate use.

Yet a further object of the present invention is to provide a method for performing anastomotic surgery utilizing anastomotic ring members and a coupling tube.

These and other objects of the present invention will become more apparent after consideration of the following detailed specification taken in conjunction with the accompanying drawings wherein like characters of reference designate like parts throughout the several views.

FIGURE DESCRIPTION

DESCRIPTION OF A PREFERRED EMBODIMENT

Figure 7:
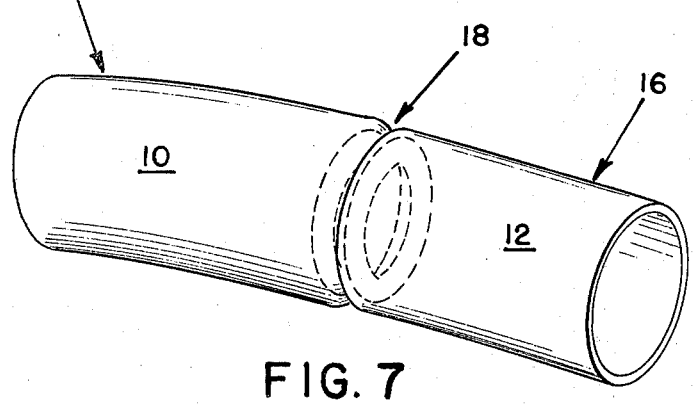
FIG. 7 is a perspective, fragmentary view of the completed anastomosis shown in FIG. 6.

Referring now to the drawings and particularly to FIG. 7, free ends 10 and 12 of two tubular tissue members, shown here as cut edges of intestinal tracts and referred to generally as 14 and 16, have been anastomosed by using apparatus comprising the present invention shown by broken lines in outline form and designated generally as 18.

Figure 1:
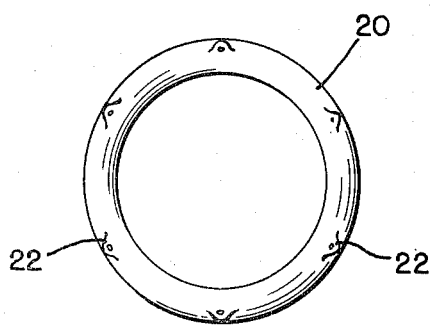
FIG. 1 is a plan view of an anastomotic ring member comprising part of the present invention having fenestrated projections about its periphery.

A basic component of device 18 is the anastomotic ring member 20 shown in FIG. 1 which has a plurality of fenestrated projections 22 spaced (preferably evenly) about one surface of the member's periphery. Smooth ridges 24 are incorporated on the other surface about the member's periphery to prevent excessive pressure on the tissue wall thus occluding blood circulation.

Figure 4:
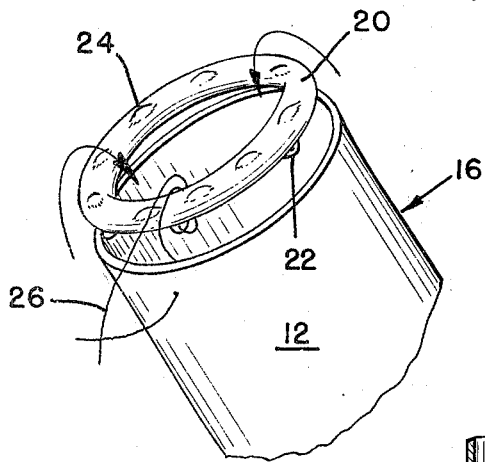
FIG. 4 is a perspective, fragmentary view of an anastomotic ring member being affixed to the free end of a tubular tissue member by suture material.
Figure 5:
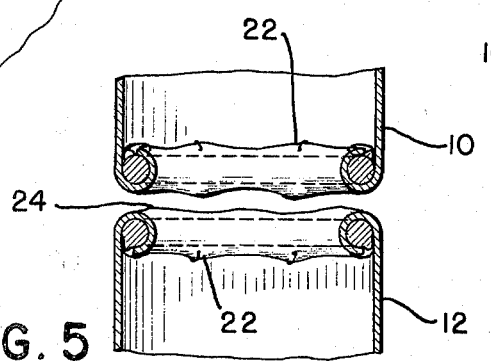
FIG. 5 is a cross-sectional, side-elevational view of a pair of anastomotic ring members inserted in each free or open end of two tubular tissue members which have been pulled over the outside and through the inside of the ring members.

Ring member 20 is attached to free end 12 of tubular tissue member 16. This is done by pulling the free end over the outside of ring member 20 with the ring positioned so that the fenestrated projections are directed into the opening. Suture material 26 is passed through the tissue wall through the inside of the ring and fenestrated projections 22 as shown in FIG. 4. As the suture material is tightened, the tissue edge slides completely over the outside of the ring member and through the inside of the ring member so that it is inverted as shown in FIG. 5.

Figure 3:
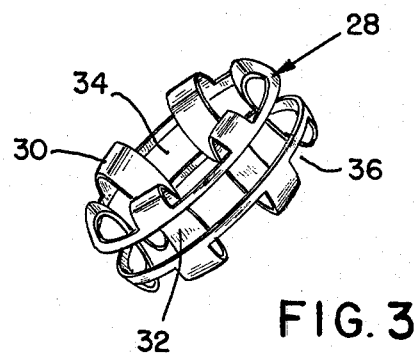
FIG. 3 is a perspective view of the coupling tube comprising a part of the present invention having convex outer surfaces and concave inner surfaces with an opening through the middle for passage of fluid or other substances.
Figure 2:
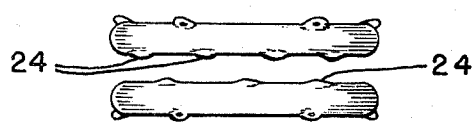
FIG. 2 is a side elevational view of the pair of anastomotic ring members like that shown in FIG. 1 showing fenestrated projections on one surface and smooth ridges on the other surface to prevent excessive pressure on tissue walls.

The coupling tube 28 is shown perspectively in FIG. 3 and has a convex outer surface 30, a concave inner surface 32, and an opening 34 substantially coincident with its longitudinal axis. A plurality of elongated openings 36 are positioned within the coupling tube wall and facilitates flexing of the component when this becomes necessary.

Figure 6:
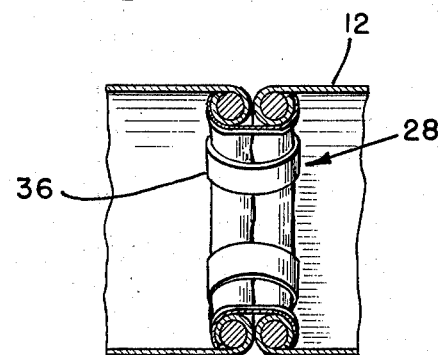
FIG. 6 is a cross-sectional, side elevational view of a completed anastomosis utilizing the apparatus of the present invention.

When both free ends have been provided with a ring member as previously described (see FIG. 5), coupling tube 28 is passed through each of the anastomotic ring members and assumes the position shown in FIG. 6 wherein its concave surface engages the sides of the ring members from which the fenestrated projections are located.

Preferably, the anastomotic rings and coupling tube are made of a composite material which can be fashioned to disintegrate in a given period of time. The bulk of these components is composed of nonabsorbable small pieces of elements agglutinated by a thin layer of absorbable material soluble within the lumen of the intestine.

The present invention offers many advantages over conventional anastomosis and permits simple, rapid anastomosis in difficult areas. For example, it permits a simple anastomosis in a low rectosigmoid anastomosis which would ordinarily be quite time-consuming and difficult, or impossible, in those cases necessitating a colostomy.

In conclusion, it will be apparent that the invention is comprised basically of anastomotic ring members and a coupling tube, both of which may take the form of the embodiment described herein. However, the invention in its broader aspects is not limited to the specific embodiment herein shown and described but departures may be made therefrom within the scope of the accompanying claims without departing from the principles of the invention and without sacrificing its chief advantages.

I claim:

1. Apparatus for intestinal anastomosis comprising: a pair of separate anastomotic ring members for securement each to the free end of the two tubular tissue members to be anastomosed, each having interior and exterior surfaces; and a separate annula coupling time for securing each ring member and attached tissue member to the other ring member and attached tissue member, the tissue member ends being contiguously inverted to enable the ends to grow together permanently and approximate the outer surface of the intestine, and each of said ring members having a plurality of fenestrated projections and further comprising means connecting said ring member projections to the tissue member ends, said coupling tube having a convex outer surface, a concave inner surface, and an opening substantially defined by said convex outer surface, said coupling tube concave surface engaging each of said ring members proximate said fenestrated projection, said coupling tube wall carrying a plurality of elongated openings therein.

2. The apparatus of claim 1 wherein said ring members and said coupling tube are formed of disintegrable materials.

3. A method of performing intestinal anastomotic surgery utilizing a pair of separated anastomotic ring members and a separate coupling tube comprisng the steps of: securing a ring member to the free end of one of the two tubular tissue members to be joined after inverting the free end over and about the ring member; and securing each ring member and invertedly attached tissue member to the other ring member and invertedly attached tissue member with the annula coupling tube to enable the tissue member ends to grow together permanently near the member ends and approximate the outer surface of the intestine, the annula coupling tube being secured around the member ends internally of the ring members after the member ends have been pulled over the outside and through the inside of the ring members.

* * * * *